(12) United States Patent
Fadler

(10) Patent No.: US 8,031,832 B2
(45) Date of Patent: Oct. 4, 2011

(54) CIRCULAR MULTI-BEAM X-RAY DEVICE

(75) Inventor: Franz Fadler, Hetzles (DE)

(73) Assignee: Siemens Aktiengesellschaft, Munich (DE)

( * ) Notice: Subject to any disclaimer, the term of this patent is extended or adjusted under 35 U.S.C. 154(b) by 53 days.

(21) Appl. No.: 12/572,397

(22) Filed: Oct. 2, 2009

(65) Prior Publication Data

US 2010/0091939 A1   Apr. 15, 2010

(30) Foreign Application Priority Data

Oct. 2, 2008   (DE) .......................... 10 2008 050 353

(51) Int. Cl.
  *H05G 1/60*   (2006.01)
  *H01J 35/08*   (2006.01)
  *G21K 1/04*   (2006.01)

(52) U.S. Cl. ........................... 378/21; 378/124; 378/150

(58) Field of Classification Search ............. 378/4, 9.19, 378/16, 21, 124, 145–153, 136, 143
See application file for complete search history.

(56) References Cited

U.S. PATENT DOCUMENTS

| | | | |
|---|---|---|---|
| 4,489,426 A * | 12/1984 | Grass et al. | 378/150 |
| 6,980,627 B2 | 12/2005 | Qiu et al. | |
| 7,192,031 B2 * | 3/2007 | Dunham et al. | 378/122 |
| 7,359,484 B2 * | 4/2008 | Qiu et al. | 378/122 |
| 2007/0172024 A1 | 7/2007 | Morton et al. | |
| 2009/0003525 A1 * | 1/2009 | Gertner et al. | 378/65 |

* cited by examiner

*Primary Examiner* — Irakli Kiknadze
(74) *Attorney, Agent, or Firm* — Schiff Hardin LLP

(57) ABSTRACT

A multi-beam x-ray device has a multi-beam x-ray tube with an interior in the form of a circle. Focal spots of the x-ray radiation are arranged along the circle. An x-ray tube control unit controls the x-ray radiation emission such that an x-ray beam is emitted from each segment of the circle in specified sequence. The circle is divided up into at least two segments, and multiple diaphragms, each with at least one diaphragm aperture therein, one mounted to rotate around the center point of the circular path into the beam path of the x-ray tube. A first diaphragm, whose first diaphragm aperture limits the cross section of the x-ray beam emitted from the x-ray tube, is associated with each segment of the circular path. A number of slice images can be acquired without a movement of the x-ray tube.

6 Claims, 2 Drawing Sheets

CIRCULAR MULTI-BEAM X-RAY DEVICE

BACKGROUND OF THE INVENTION

1. Field of the Invention

The present invention concerns a multi-beam x-ray device of the type having multi-beam x-ray tube and a diaphragm arrangement for fast acquisition of a plurality of x-ray images.

2. Description of the Prior Art

Conventional x-ray tubes are essentially composed of a vacuum chamber with housing in which a cathode and an anode are enclosed. The cathode acts as a negative electrode that emits the electrons toward the positive anode. The electrons are attracted from the anode and strongly accelerated by an electrical field between anode and cathode. The anode typically is formed of a metal, for example tungsten, molybdenum or palladium. When the electrons bombard the anode, their energy is for the most part converted into heat. Only a fraction of the kinetic energy can be converted into x-ray photons that are emitted by the anode in the form of an x-ray beam. The x-ray beam that is generated in such a manner exits the vacuum chamber through a radiation-permeable window made of a material with low atomic number.

Applications in industrial and medical imaging and for therapeutic treatments are unimaginable without x-ray tubes. All imaging methods with x-rays utilize the fact that different materials absorb x-rays differently. Conventional x-ray imaging methods generate a two-dimensional projection of a three-dimensional projection of a three-dimensional subject. The spatial resolution along the propagation direction of the x-ray beam is thereby lost.

Although it is also based on the different x-ray absorption properties of different materials, computed tomography offers a different form of imaging known as a slice image method. In computed tomography multiple x-ray images of a subject are generated from different directions and the lost volume information is subsequently reconstructed from these multiple images using a technique known as a back-projection method. Normally these 3D reconstructions are assembled from individual slices that proceed transverse to the subject. In this way a density can be determined for every volume element of the subject (known as a voxel, which corresponds to a three-dimensional pixel). A 3D image inside the subject can therefore be generated from all voxels.

In order to generate the multiple different slice images in computed tomography, an x-ray tube emitting the x-rays and an x-ray detector receiving the x-rays after exposure of the subject are moved around the subject. The mechanical movement is complicated and also occupies valuable examination time in medical technology. Various approaches have therefore been developed in order to be able to emit multiple different radiation beams from an x-ray tube. It is the goal to generate many slice images with different observation angles without mechanically moving the x-ray tube and the x-ray detector.

The PCT Application WO 25 2004/110111 A2 specifies a promising solution. A multi-beam x-ray tube with a stationary field emission cathode and an opposite anode are disclosed by this. The cathode comprises a plurality of stationary, individually controllable electron-emitting pixels that are distributed in a predetermined pattern on the cathode. The anode has a number of focal spots that are arranged in a predetermined pattern that is executed corresponding to the pattern of the pixels. A vacuum chamber encloses the anode and cathode. In one development, the cathode comprises carbon nanotubes.

The solution disclosed in WO 2004/110111 A2 offers many advantages relative to conventional thermionic x-ray radiation sources. It eliminates the heating element of the anode, operates at room temperature, generates pulsed x-ray radiation with a high repetition rate and generates plurality of beams with different focal spots.

In order to be able to use multi-beam x-ray tubes in medical technology, for example for a tomosynthesis in mammography, numerous adaptations are required. Among other things, it must be ensured that the radiation exposure of patients is minimized, the scatter radiation is reduced and the image series frequency is increased.

SUMMARY OF THE INVENTION

An object of the invention is to provide a multi-beam x-ray tube and a method to operate this via which a multi-beam x-ray tube can also be used in medical technology.

In accordance with the invention, a multi-beam x-ray device has a multi-beam x-ray tube in the shape of a circle, with focal spots of the x-ray radiation arranged along (around) the circle. The device also has an x-ray tube control unit that controls the x-ray radiation emission to activate the focal spots to cause an x-ray beam can be emitted from each segment of the circle in specified sequence. The circle is divided into at least two segments, and multiple first diaphragms with at least one respective first diaphragm aperture are arranged such that they can rotate around center of the circle into the beam path of the x-ray tube. A first diaphragm, whose first diaphragm aperture limits the cross section of the x-ray beam emitted from the x-ray tube, is associated with each segment of the circle. The advantage of the device is that a number of slice images can be acquired without a movement of the x-ray tube.

In an embodiment, the first diaphragm aperture can overlay the x-ray beam on an x-ray image receiver arranged in a fixed position relative to the multi-beam x-ray tube by the first diaphragm aperture rotates around its center point. The x-ray image receiver thus does not need to be moved between two acquisitions.

The first diaphragms can be controlled such that the first diaphragm from, through whose first diaphragm aperture an x-ray beam is currently passing, is located at rest while the other first diaphragms move in the direction toward a new focal spot position. This allows the x-ray image frequency to be increased without having to increase the rotation speed of the first diaphragm.

Furthermore, the device can have at least two first diaphragm apertures in each first diaphragm, and second diaphragms respectively associated with the first diaphragms. The first diaphragm aperture through which no x-ray radiation is currently passing is covered by the associated second diaphragm. The offers the advantage that no unwanted x-ray scatter radiation can escape.

In a further embodiment, the focal spots can have a regular angular separation from one another, and the angular separation of the first diaphragm apertures of the first diaphragm relative to one another can be n.5 times the angular separation of the focal spots, wherein n∈N, N being the number of focal spots. The rotation movements of the first diaphragm can thereby be minimized.

In an embodiment, a mammography system for tomosynthesis can be equipped with a multi-beam x-ray device according to the invention. Many x-ray images of the female breast can thereby be generated in a very fast series.

DESCRIPTION OF THE PREFERRED EMBODIMENTS

Figure 1:
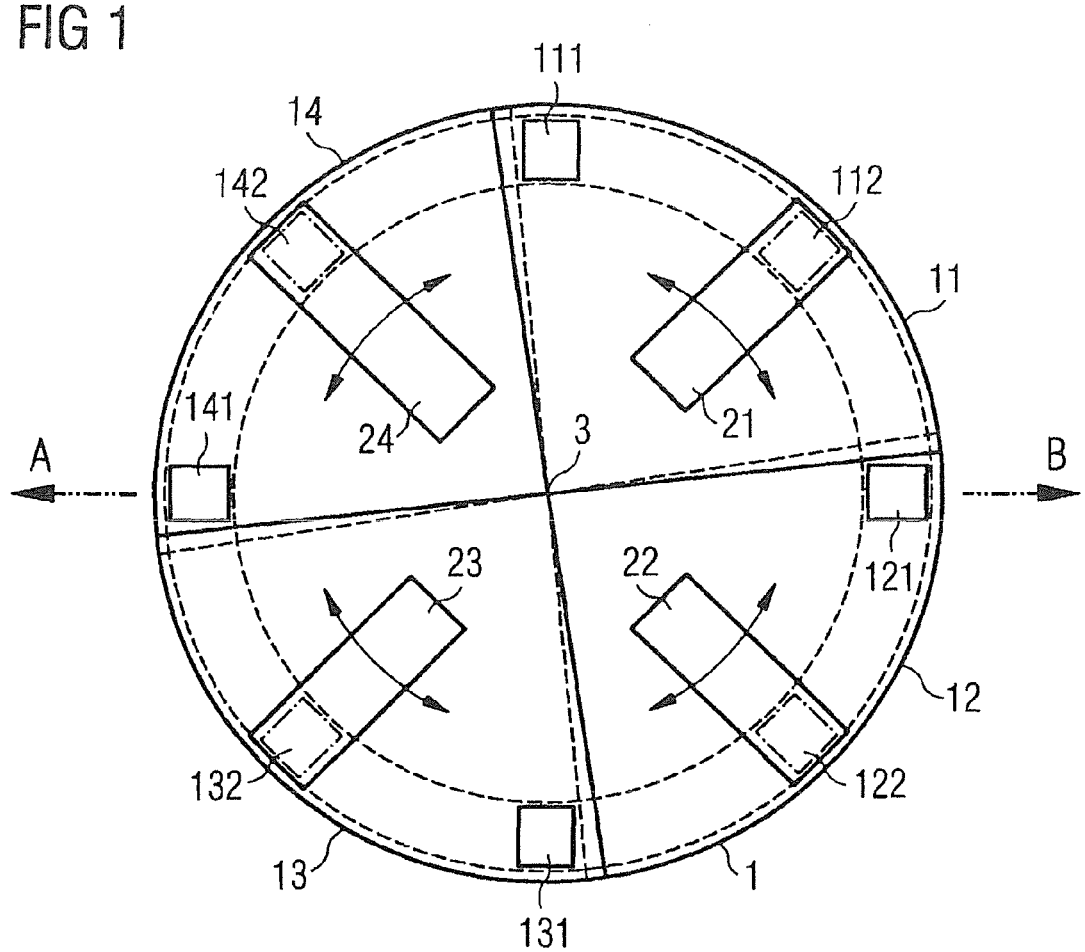
FIG. 1 is a plan view of a diaphragm arrangement of the multi-beam x-ray device according to the invention.

In FIG. 1 a view of a circular multi-beam x-ray tube 1 covered by four first diaphragms 11, 12, 13, 14 is shown from above. The focal spots (shown in FIG. 3) of the x-ray tube 1 are arranged along a circular path in the x-ray tube 1, so x-ray radiation is emitted approximately upwardly in the direction of an x-ray image detector (not shown). The first diaphragms 11, 12, 13, 14 are mounted so as to rotate around a common rotation point 3. Each is somewhat larger than a quarter-circle. Two first diaphragms 11, 13 and two first diaphragms 12, 14 are respectively arranged in different planes so that they can overlap, and therefore the escape of scatter radiation is prevented.

Each diaphragm 11, 12, 13, 14 has two first diaphragm apertures, respectively designated 111, 112, 121, 122, 131, 132, 141, 142 that limit the x-ray beam emitted by the x-ray tube 1 in terms of its cross section and map it onto the x-ray image detector. The x-ray image detector must rotate as well corresponding to the position of the first diaphragm apertures 111, 112, 121, 122, 131, 132, 141, 142 in order to maintain the same position relative to the mapped x-ray image. The first diaphragm aperture 112 of the first diaphragm 11 through which no x-ray radiation at all should escape is occluded or closed by a second diaphragm 21. Second diaphragms 22, 23, 24 are likewise associated with the other three first diaphragms 12, 13, 14. Each second diaphragm 21, 22, 23, 24 is likewise arranged such that they can rotate around the center point 3 of the circle so that they can track the positions of the first diaphragm apertures 111, 112, 121, 122, 131, 132, 141, 142. The emission of the x-ray radiation from different focal spots as well as the positions of the first diaphragm apertures 111, 112, 121, 122, 131, 132, 141, 142 and the positions of the second diaphragms 21, 22, 23, 24 are controlled by an x-ray tube control unit 3, shown in FIG. 4, so that x-ray radiation is always emitted in alternation from each circle segment of the x-ray tube 1 associated with the first diaphragms 11, 12, 13, 14, so the emission additionally jumps between the positions of the two first diaphragm apertures of each first diaphragm. Only the first diaphragm through which the x-ray radiation should escape is located at rest. The three other first diaphragms move continuously to their next required position in the intervening time. This allows the image acquisition frequency to be increased by a factor of 8 without the first diaphragms 11, 12, 13, 14 having to rotate faster. The order of the activation of 52 focal spots is shown in detail in FIG. 3.

If the x-ray image detector should not be rotated, then the first diaphragm apertures 111, 112, 121, 122, 131, 132, 141, 142 must be correspondingly rotated around their centers. The alignment of the first diaphragm apertures 111, 112, 121, 122, 131, 132, 141, 142 relative to the x-ray image receiver is also maintained given a rotation movement of the first diaphragms 11, 12, 13, 14.

Figure 2:
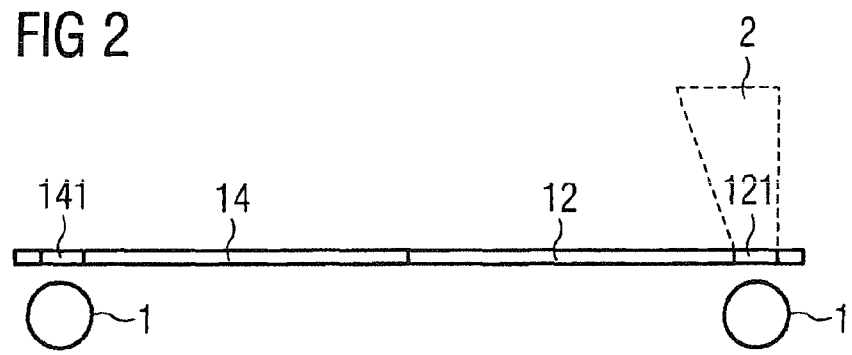
FIG. 2 is a section view of the diaphragm arrangement according to FIG. 1.

FIG. 2 shows a section from A to B through the arrangement according to the invention from FIG. 1. A multi-beam x-ray tube 1 has an interior shape of a circular path. The tube 1 can emit a number of x-ray beams approximately upwardly respectively form different focal spots. An x-ray radiation 2 with its limitation is drawn in FIG. 2. It is limited in terms of its cross section by a first diaphragm aperture 121 in a first diaphragm 12 and mapped to an x-ray image detector (not shown). The first diaphragm 14 situated opposite this with its first diaphragm aperture 141 is likewise visible in the cross section of FIG. 2. The rotation of the first diaphragm apertures 111, 112, 121, 122, 131, 132, 141, 142 around their centers can ensue with the use of an epicyclic train (belt).

The first diaphragm apertures can be of different sizes, so different dimensions can be superimposed on the x-ray image receiver.

Figure 3:
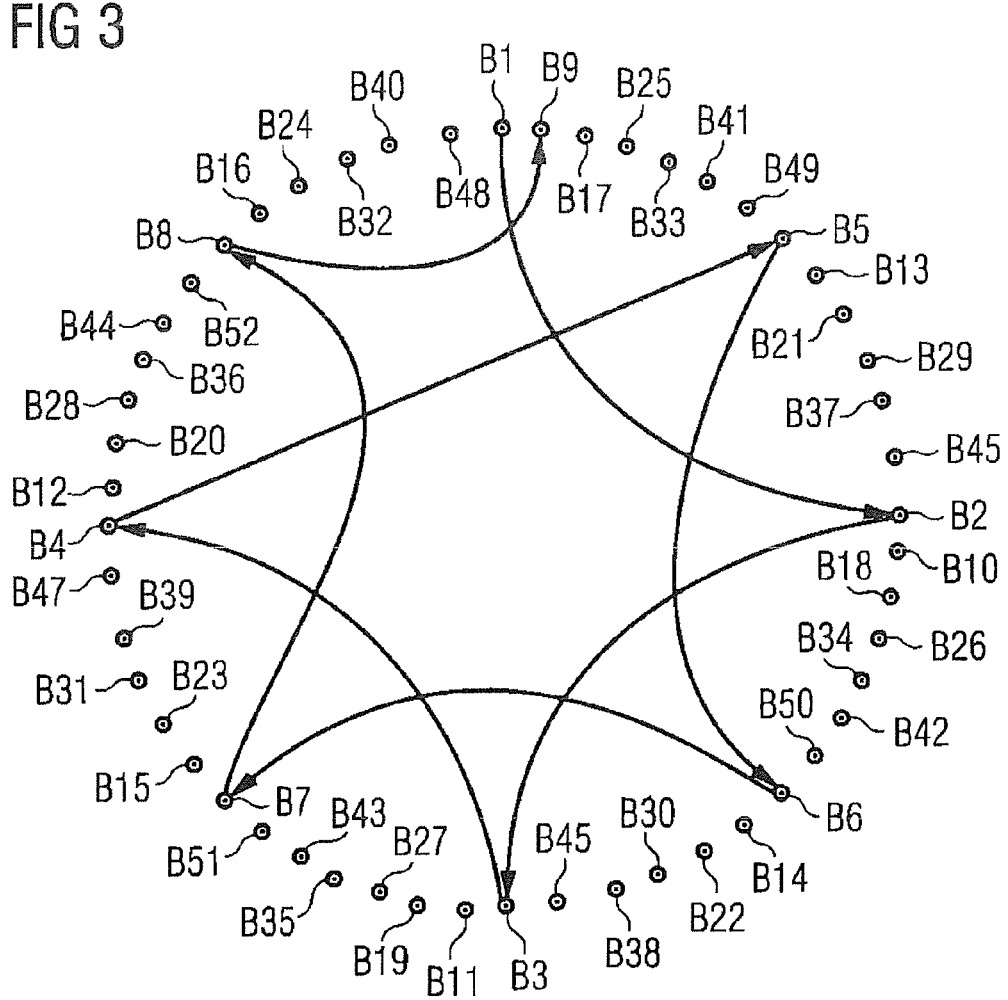
FIG. 3 is an example of a focal spot arrangement in the multi-beam x-ray tube according to the invention.
Figure 4:
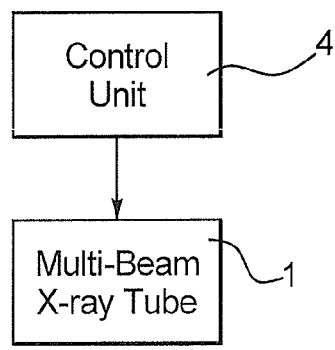
FIG. 4 schematically illustrates a multi-beam x-ray tube connected to a control unit in accordance with the present invention.

Focal spots B1 through B52 of a multi-beam x-ray tube are shown in FIG. 3. The focal spots B1 through B52 are located on a circular line and have the same respective angular separation from one another. The 52 focal spots B1 through B52 are activated by the x-ray tube control unit 4 shown in FIG. 4 to emit an x-ray beam corresponding to their numbering. The order of the first nine activated focal spots B1 through B9 are indicated with the arrows. The apparently strange order is based on the fact that, as described above with regard to FIG. 1, four first diaphragms 1 shaped as circle segments with two respective diaphragm apertures are used. The first diaphragms can be moved independently of one another. The two first diaphragm apertures are spaced apart from one another with 6.5 times the angular separation. For example, the two first diaphragm apertures thereby comes to be situated over the focal spot B5 at the correct point in time. While x-ray radiation is emitted below a first diaphragm located at rest, the three other first diaphragms move on by ⅛ the angular separation of the focal spots. The first diaphragm apertures thus reach the next focal spot after exactly two beam cycles.

The multi-beam x-ray device according to the invention can advantageously be used for a tomosynthesis in mammography. With the arrangement described above, 52 slice images can be acquired in the shortest possible time and be processed into a new spatial view.

A further preferred application is x-ray image acquisition in the operating room where movements of x-ray systems are disruptive. With the device according to the invention, x-ray radiator and x-ray detector remain at rest.

Although modifications and changes may be suggested by those skilled in the art, it is the intention of the inventor to embody within the patent warranted hereon all changes and modifications as reasonably and properly come within the scope of his contribution to the art.

I claim as my invention:

1. A multi-beam x-ray device, comprising:
a multi-beam x-ray tube having an interior circle and a plurality of focal spots, from which x-rays are respectively emitted, located along said circle, said circle being comprised of segments;
an x-ray tube control unit that controls emission of x-rays from said multi-beam x-ray tube by activating emission of x-rays from individual ones of said focal spots to cause an x-ray beam to be emitted from respective focal spots; and
a plurality of x-ray beam diaphragms located relative to said multi-beam x-ray tube respectively in each segment, each of said diaphragms comprising a diaphragm plate having a diaphragm aperture therein that limits the respective x-rays emitted from the respective focal spots, and mounted for rotation around a center of said circle, to place the diaphragm aperture in a path of the x-rays emitted by a currently-activated focal spot in the segment in which the diaphragm is located each diaphragm limiting the x-rays in said path to produce an x-ray beam that exits said x-ray tube.

2. A multi-beam x-ray device as claimed in claim 1 comprising an x-ray image receiver that detects the x-ray beams emitted from the respective focal spots of the multi-beam x-ray tube, said x-ray image receiver being fixed relative to said multi-beam x-ray tube, and each diaphragm aperture overlying said x-ray image receiver.

3. A multi-beam x-ray device as claimed in claim 1 wherein said control unit is configured to control the rotation units of the respective diaphragms to cause a diaphragm plate in front of a currently-activated focal spot to be at rest, while simultaneously moving at least one other diaphragm plate at another of said polygon sides to a position in front of a focal spot to be subsequently activated in said specified sequence.

4. A multi-beam x-ray device as claimed in claim 1 wherein each of said diaphragm plates is a first diaphragm plate that has two first diaphragm plate apertures therein, and wherein only one of said two first diaphragm apertures is in the path of the x-rays emitted by the currently-activated focal spot at a time, and each diaphragm comprising a second diaphragm plate that covers the diaphragm aperture in the first diaphragm plate that is not in the path of the x-rays emitted by the currently-activated focal spot.

5. A multi-beam x-ray device as claimed in claim 4 comprising N focal spots, and wherein said focal spots are located along said circle with a uniform angular separation between neighboring focal spots, and wherein said diaphragm apertures in each first diaphragm plate are spaced from each other by a plate spacing that is n.5 times the angular separation between neighboring focal spots, wherein n∈N.

6. A multi-beam x-ray device as claimed in claim 1 wherein said control unit is configured to activate said focal spots in a sequence that causes a tomosynthetic image to be generated upon detection of the respective x-ray beams from the respective focal spots.

* * * * *